United States Patent
Gordon

(10) Patent No.: US 7,292,889 B2
(45) Date of Patent: Nov. 6, 2007

(54) GASTRIC STIMULATOR APPARATUS AND METHOD FOR USE

(75) Inventor: Pat L. Gordon, Wyzata, MN (US)

(73) Assignee: Medtronic Transneuronix, Inc., Mt. Arlington, NJ (US)

( * ) Notice: Subject to any disclaimer, the term of this patent is extended or adjusted under 35 U.S.C. 154(b) by 519 days.

(21) Appl. No.: 10/999,515

(22) Filed: Nov. 30, 2004

(65) Prior Publication Data

US 2005/0113880 A1 May 26, 2005

Related U.S. Application Data

(62) Division of application No. 09/466,387, filed on Dec. 17, 1999, now Pat. No. 6,895,278.

(60) Provisional application No. 60/129,209, filed on Apr. 14, 1999.

(51) Int. Cl.
*A61N 1/36* (2006.01)
(52) U.S. Cl. .......................... 607/40; 607/59
(58) Field of Classification Search .................. 607/40, 607/41, 45, 59
See application file for complete search history.

(56) References Cited

U.S. PATENT DOCUMENTS

| | | | |
|---|---|---|---|
| 5,188,104 A | * | 2/1993 | Wernicke et al. ............. 607/40 |
| 5,423,872 A | | 6/1995 | Cigaina |
| 6,041,258 A | | 3/2000 | Cigaina et al. |
| 6,542,776 B1 | | 4/2003 | Gordon et al. |
| 6,606,523 B1 | | 8/2003 | Jenkins |

FOREIGN PATENT DOCUMENTS

WO WO98/53878 12/1998

* cited by examiner

*Primary Examiner*—Kennedy J. Schaetzle

(57) ABSTRACT

Apparatus and method for stimulating neuromuscular tissue in the stomach. The neuromuscular stimulator stimulates the neuromuscular tissue by applying current-controlled electrical pulses. A voltage sensor detects the voltage across the neuromuscular tissue to determine if the voltage meets a predetermined voltage threshold. A control circuit adjusts the current-controlled pulse if the voltage is found to meet the voltage threshold, such that the voltage does not exceed the voltage threshold. A voltage-controlled pulse may also be applied to the tissue. A current sensor would then detect whether the current on the neuromuscular tissue meets a predetermined current threshold, and a control circuit adjusts the voltage-controlled pulse such that the current does not exceed the current threshold. A real time clock may be provided which supplies data corresponding to the time of day during the treatment period. A programmable calendar stores parameters of the stimulating pulse, wherein the parameters have a reference to the time of day.

29 Claims, 9 Drawing Sheets

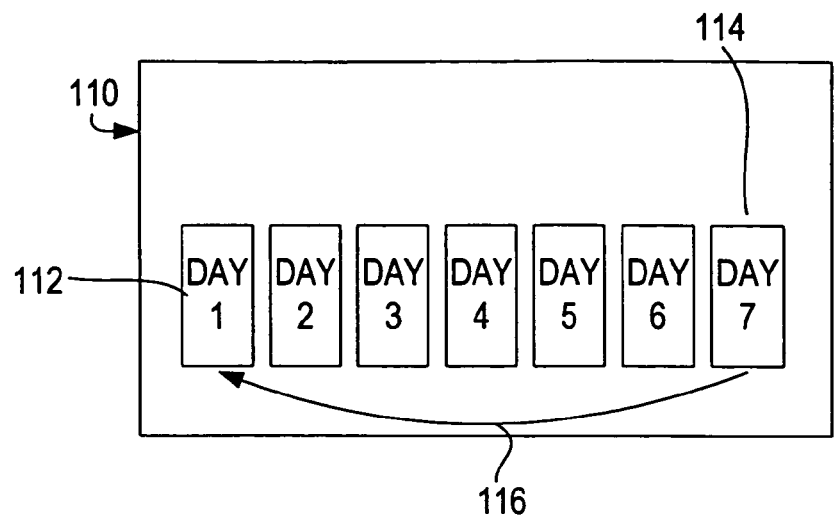
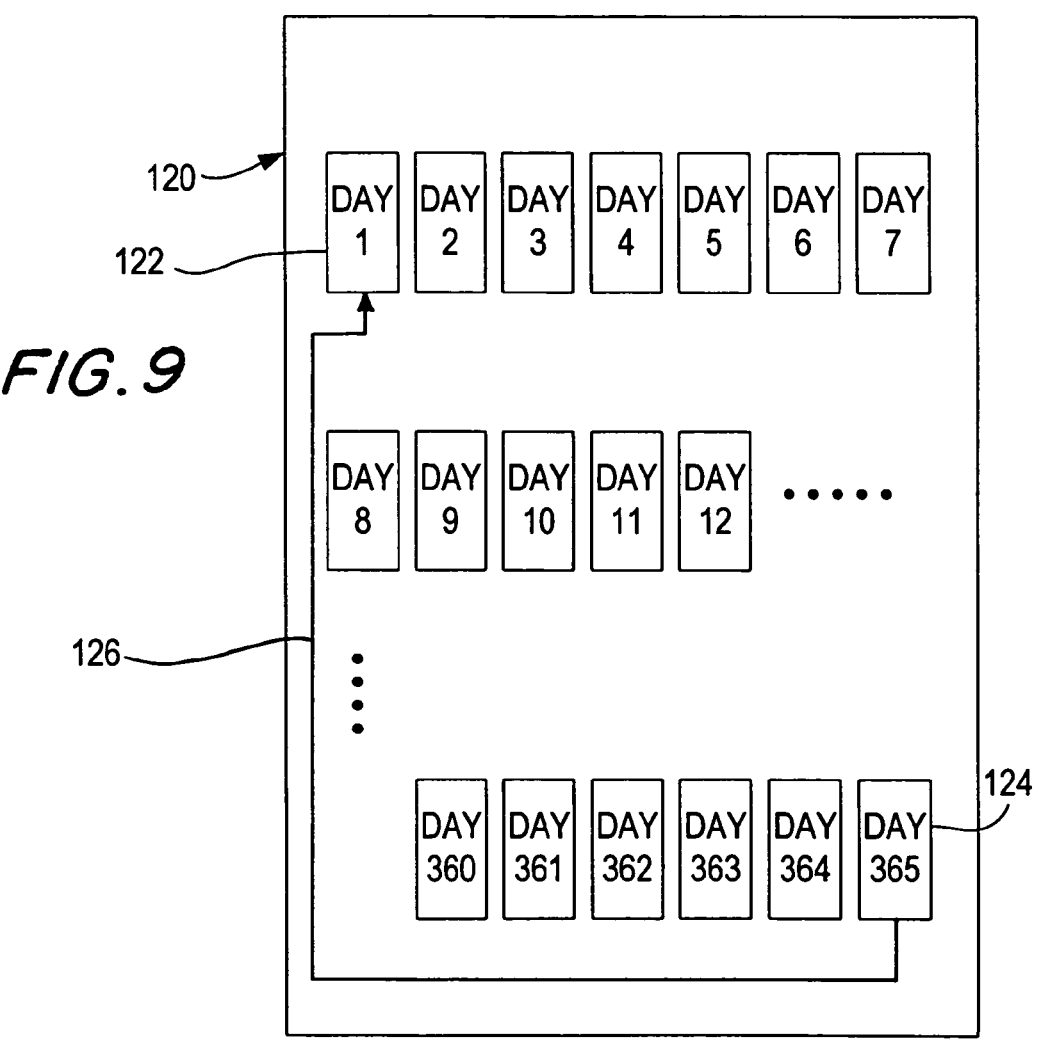

GASTRIC STIMULATOR APPARATUS AND METHOD FOR USE

CROSS-REFERENCE TO RELATED APPLICATION

This application is a divisional of U.S. patent application Ser. No. 09/466,387, filed on Dec. 17, 1999, now U.S. Pat. No. 6,895,278 which claims the benefit of U.S. Provisional Application No. 60/129,209, filed Apr. 14, 1999 and is incorporated by reference in its entirety herein.

BACKGROUND OF THE INVENTION

This invention relates to electrical stimulation apparatus and methods for use in stimulating body organs, and more particularly to implantable apparatus and methods for periodic electrical gastric stimulation.

The field of electrical tissue stimulation has recently been expanded to include devices which electrically stimulate the stomach with electrodes implanted in the tissue. These gastric stimulators have been found to successfully combat obesity in certain studies. Medical understanding as to how this treatment functions to reduce obesity is currently incomplete. However, patients successfully treated report achieving normal cycles of hunger and satiation.

An apparatus and treatment method for implementing this therapy was described in U.S. Pat. No. 5,423,872 to Dr. Valerio Cigaina, which is hereby incorporated by reference in its entirety herein. The apparatus described in the Cigaina patent stimulates the stomach antrum pyloricum with trains of stimulating pulses during an interval of about two seconds followed by an "off" interval of about three seconds.

Current pacemaker design incorporates a number of features useful for the type of tissue or organ being stimulated. Pacemakers stimulating cardiac or neurological tissue, for example, may typically contain an accurate, drift-free crystal oscillator to carry out real-time functions such as pulse generation. In particular, some cardiac pacemakers use a time reference to keep track of the time-of-day with a 24-hour clock in order to log data or to vary pacing parameters during the 24-hour cycle. Similarly, neurological stimulators, such as a neurological stimulator manufactured by Cyberonics, may use the time-of-day as a reference to deliver one or more periods of pulse-train stimulation (typically lasting a few minutes each) to the vagus nerve to treat epilepsy.

The design and operation constraints for a gastric pacemaker, or stimulator, are substantially different from those for a cardiac pacemaker or a neurological pacemaker, for example. With a gastric stimulator for weight loss, size is less of a concern because of the large anatomy associated with obesity. However, a long operating life for an implantable device remains an important feature, given the significantly higher current drain required by this therapy compared to cardiac pacing. Since the implantable pulse generator may be located subcutaneously in the abdominal wall, it is feasible to use a larger device, including a larger, longer-life battery.

Moreover, stomach stimulation may require different levels and cycles of stimulation than that required for cardiac stimulation or nerve stimulation. In a neuromuscular stomach generator, for example, power consumption can be five to seven times higher than for a cardiac pacemaker. Maintaining the proper energy level for stimulation may place energy demands on the life of the battery. The characteristics of entrainment of the stomach tissue may require cycling of the electrical stimulation in more complex schedules than that previously required. Observations of early human implants have shown a surprising increase in the impedance of the electrode tissue interface, from about 700 ohms at time of implant to 1300 ohms after only as much as three months of implants. With constant current and increased impedance, voltage drain on the battery may be unacceptably high.

Thus, there is a need to optimize the operation of gastric pacemakers, or stimulators, so as to provide a longer life for the device, and hence, a longer duration of therapy without the need for repeated surgical procedures.

It is an advantage to provide an apparatus and method of stimulation wherein voltage or current can be controlled to extend the useful life of a battery used therein.

It is also an advantage of the invention to provide an apparatus and method of stimulation that is able to calculate and store data parameters to improve the levels of stimulation based on operating conditions.

It is a further advantage of the invention to provide a clock function which allows the stimulation cycles of the tissue to be programmed and executed on long term basis.

SUMMARY OF THE INVENTION

These and other advantages of the invention are accomplished by providing apparatus and methods for stimulating neuromuscular tissue of the gastrointestinal tract by applying an electrical pulse to the neuromuscular tissue. The electrical pulse applied to the tissue may be a current-controlled pulse or a voltage-controlled pulse as deemed appropriate by one skilled in the art. In the case of a stimulator applying a current-controlled pulse, the stimulator may include a voltage sensor to sense the voltage across the neuromuscular tissue being stimulated. A voltage threshold is determined by the circuitry. In a preferred embodiment, the voltage threshold may be adjustable and may be a function of the level of current applied to the tissue being stimulated.

The circuitry compares the sensed voltage and the predetermined voltage threshold. If the sensed voltage is found to meet or to exceed the predetermined voltage threshold, the circuitry will adjust the current-controlled pulse such that the sensed voltage does not exceed the predetermined voltage threshold. In a preferred embodiment, this may be accomplished by generating an error signal between the sensed voltage and the voltage threshold by using negative feedback control. The occurrence of the sensed voltage meeting or exceeding the predetermined voltage threshold may be stored as an "event", along with time at which the event occurred during the pulse interval and/or during the treatment period.

The circuitry also provides the capability of utilizing the data that is obtained during the sensing and feedback functions. For example, the total impedance may be calculated from the voltage and current values. One component of the impedance may be the electrode resistance, and the second component may be the polarization capacitance. The electrode resistance may be obtained by dividing the voltage by the controlled current. The capacitance may be obtained from the current divided by the time rate of change of the voltage. The calculated values of the resistance and the capacitance may be stored on a memory device or displayed on a display device, or used in the feedback process to determine the increment of adjustment to the current-controlled pulse.

The neuromuscular stimulator may also include a real time clock and a programmable calendar for tailoring the stimulating waveform parameters over the treatment period. The real time clock supplies data corresponding to the time of day during the treatment period. The programmable calendar stores parameters which refer to the shape of the stimulating waveform. Each of the parameters may be referenced directly or indirectly to the time of day. Circuitry, such as a control circuit, applies the stimulating pulses which are defined by the parameters at the appropriate times of the day during the treatment period.

In a preferred embodiment, the parameter may be a time period during which the electrical pulses are applied. The time period may be defined by a start time and a duration. When the time period is so defined, the circuit may apply the stimulating pulse beginning at the start time and continuing for the specified duration. The time period may alternatively be defined by a start time and a stop time. In such a case, the circuit applies the stimulating pulse beginning at the start time, and continues to apply the pulses until the stop time. According to another embodiment, the time period may be defined by a start time, a first duration with respect to the start time, and a second duration with respect to the first duration. The circuit may apply the stimulating pulse beginning at the start time and continuing for the first duration, and subsequently discontinuing the pulses during the second duration. Additional parameters may be a time period corresponding to the pulse width for each pulse during the series of electrical pulses, and a time period corresponding to the pulse interval between each pulse. A parameter may also include a voltage corresponding to the pulse height for each pulse in the series of electrical pulses.

The real time clock and the programmable calendar allow the stimulating waveform to vary over greater periods of time. For example, the real time clock may supply data corresponding to a week during the time period. Consequently, the waveform may be programmed to apply a different waveform during each particular week in the treatment period. The real time clock may also supply data corresponding to the day of the week during the treatment period. Alternatively, the real time clock may supply data corresponding to a month of the year during the treatment period, such that the waveform may vary from month-to-month as the treatment progresses. Moreover, the real time clock may also supply data corresponding to the day of the month, and/or the day of the year.

Although current-controlled stimulating pulses are described above, the invention is equally applicable to constant voltage and voltage-controlled pulses.

Further features of the invention, its nature and various advantages will be more apparent from the accompanying drawings and the following detailed description of the preferred embodiments.

BRIEF DESCRIPTION OF THE DRAWINGS

FIG. 6(*b*) is a time plot illustrating a prior art voltage wave form corresponding to the time plot of FIG. 6(*a*).

FIG. 6(*c*) is a time plot illustrating a voltage wave form corresponding to the time plot of FIG. 6(*a*) in accordance with the invention.

FIG. 8 illustrates another data structure in accordance with the invention.

FIG. 9 illustrates yet another data structure in accordance with the invention.

DETAILED DESCRIPTION OF THE PREFERRED EMBODIMENT

Figure 1:
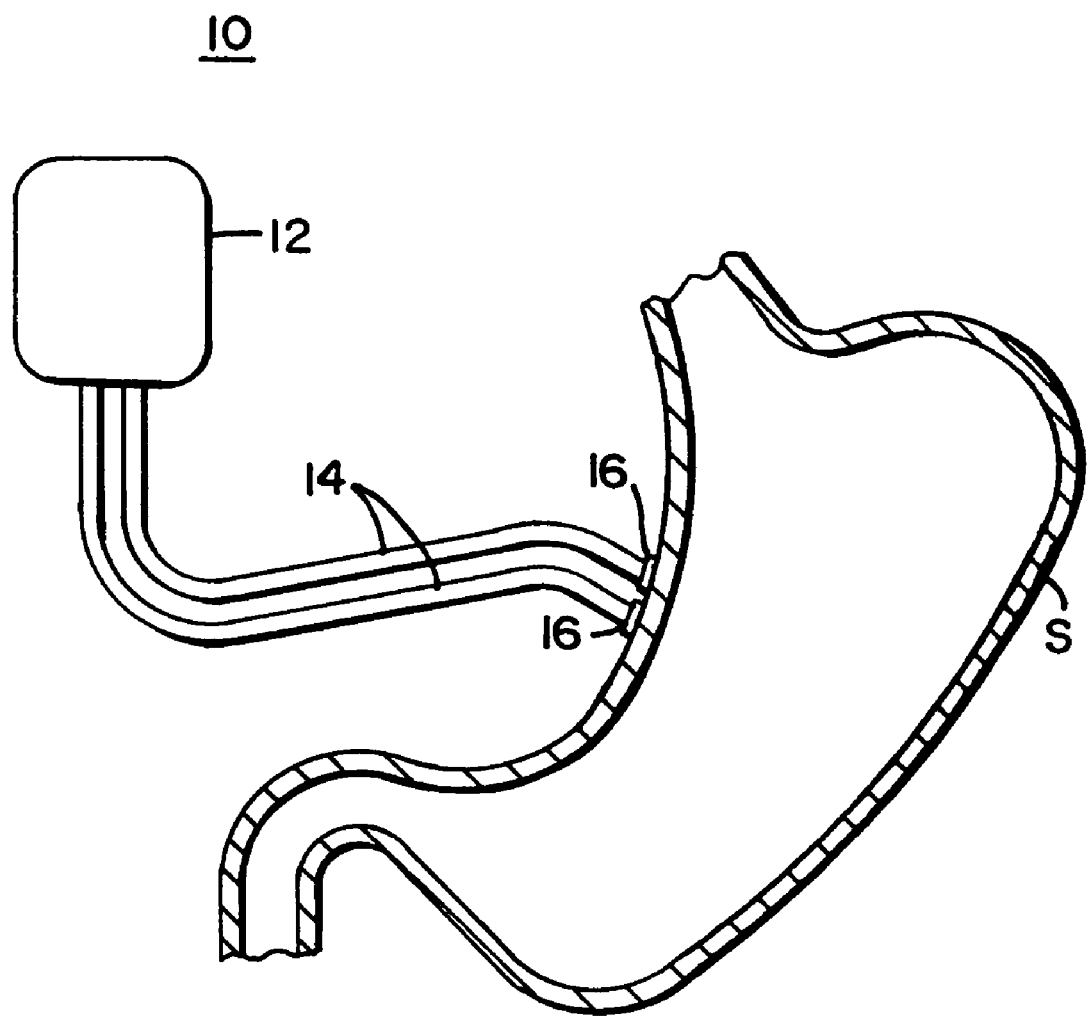
FIG. 1 is a simplified view of a preferred embodiment in accordance with the invention.

An improved neuromuscular stimulator is illustrated in FIG. 1, and designated generally with reference number 10. The stimulator 10 includes an implantable pulse generator 12, a lead system 14 of one or more electrodes 16. Stimulator 10 may use voltage controlled and/or current controlled stimulation in such a way to limit power drains from the battery and to allow accurate determination of total impedance, including lead resistance and polarization capacitance. Consequently, maintaining substantially consistent levels of power consumption may dramatically improve longevity. Stimulator 10 may limit changes in power consumption and may store data, which may be provided to the clinician or used to vary stimulation parameters. For example, stored data may include the occurrences of a voltage and/or current limitation during a stimulation pulse. Measured parameters may be stored to correlate stimulation levels with operating conditions in order to maintain consistent power consumption, as will be described in greater detail hereinbelow.

The implantable pulse generator 12 provides a series of electrical pulses to the stomach S. The implantable pulse generator 12 may be surgically implanted subcutaneously in the abdominal wall. The electrodes 16 may be installed in contact with the tissue of the stomach. Electrodes may be positioned on the outer surface of the stomach, implanted within the stomach wall, or positioned on the inner surface of the stomach wall. For example, the electrodes may be attached to the tissue by an electrocatheter as described in U.S. Pat. No. 5,423,872 to Cigaina, incorporated by reference above. Alternatively, the electrodes may be as described in copending U.S. Application PCT/US98/1042 filed on May 21, 1998, and copending application Ser. No. 09/122,832, filed Jul. 27, 1998, both of which are incorporated by reference in their entirety herein. As yet another alternative, electrodes may be substantially as described in U.S. patent application Ser. No. 09/466,532 (now U.S. Pat. No. 6,606,523) and U.S. patent application Ser. No. 09/466,731 (now U.S. Pat. No. 6,542,776), both of which were filed on Dec. 17, 1999 and are incorporated by reference in their entirety herein.

Figure 2:
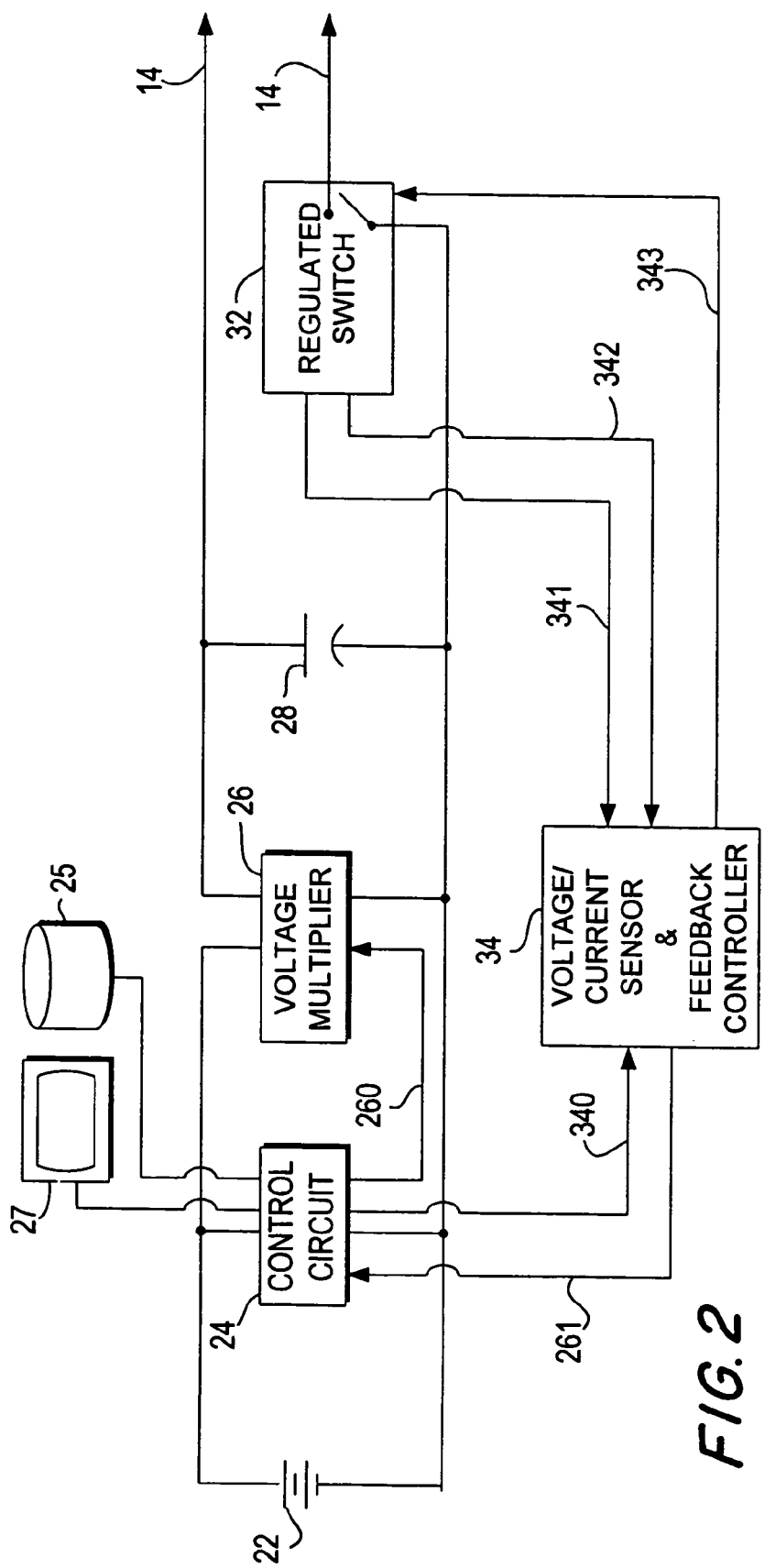
FIG. 2 is a simplified schematic view of a component of the apparatus of FIG. 2 in accordance with the invention.

A preferred embodiment of a current-controlled and/or voltage-controlled stimulator circuit according to the present invention is illustrated in FIG. 2, and hereinafter referred to as I/V circuit 20. I/V circuit 20 may typically be housed in implantable pulse generator 12. IV circuit 20 may limit power drains from the battery 22 and allow accurate determination of total impedance, including lead resistance and polarization capacitance.

The I/V circuit 20 also includes a control circuit 24, a voltage multiplier 26, storage capacitor 28, a regulated switch 32, and a voltage and/or current sensor and feedback controller 34 to regulate switch 32. The stomach tissue stimulation occurs on leads 14, which are in turn connected to electrodes 16 (FIG. 1). Moreover, memory 25 may be provided to store data, and display unit 27 for displaying data may be provided.

The battery 22 may be selected in order to have long life characteristics when implanted in the patient. The voltage-control and current-control features of the invention may extend battery life further. Preferably, the battery 22 has deliverable capacity of greater than 2.5 amp-hours. In a preferred embodiment, two batteries may be provided.

The regulated switch 32 is designed to control current and/or voltage levels either throughout the entire output stimulator pulse, e.g., by using continuous feedback, or only at the leading edge, e.g., by selecting the appropriate initial voltage on capacitor 28 based on $V_c = V_{control}$ or $V_c = I_{control} \cdot R_{electrode}$.

The shape of the current and/or voltage waveform applied to the stomach tissue is adjustable and controlled by digital means in the control circuit 24, which typically is or contains a microprocessor.

Figure 3:
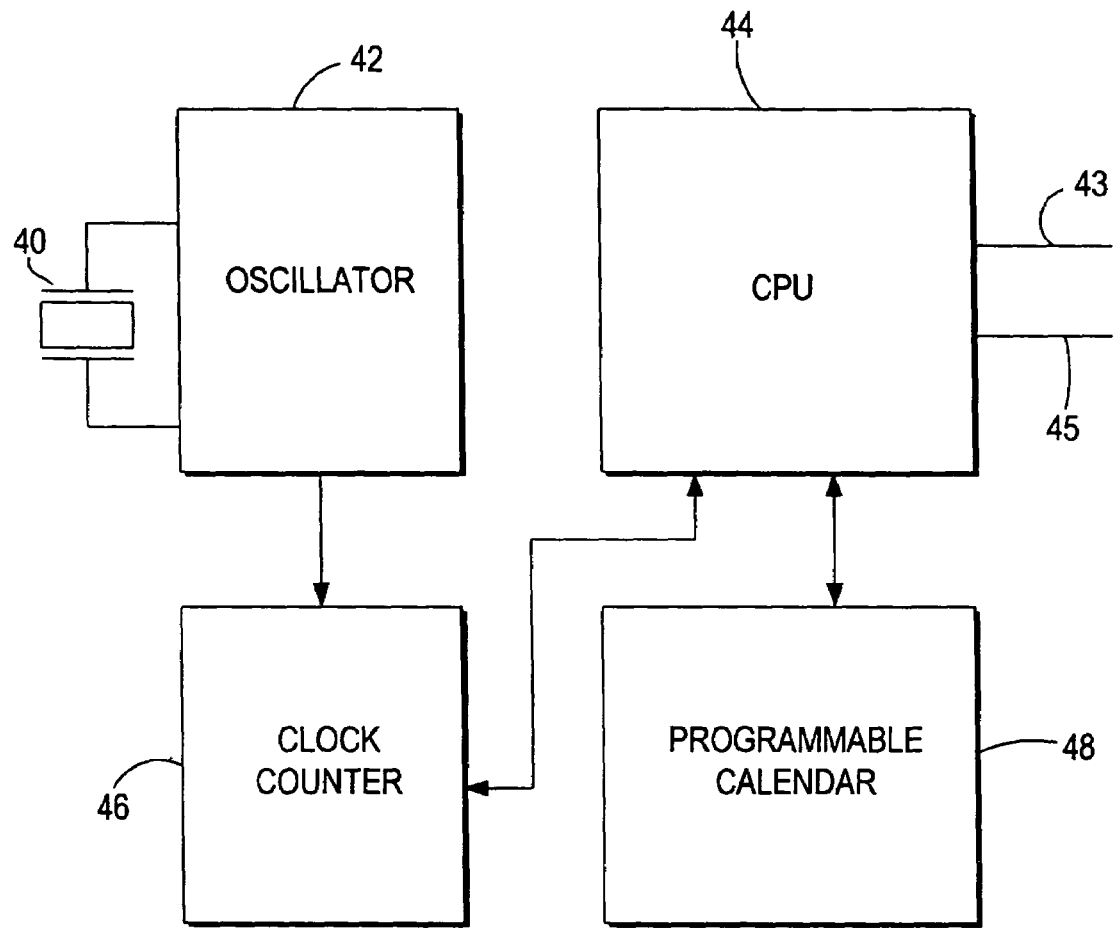
FIG. 3 is a simplified schematic view of a component of the apparatus of FIG. 3 in accordance with the invention.

The timing features of control circuit 24 are illustrated in FIG. 3. By using a crystal 2 to control oscillator 42 (which is either internal or external of processor 44 which may receive input 43 from control circuit 24 or provide output 45), accuracy is achieved for real-time clock counter 46. Alternatively, the oscillator 2 and count down chain can also be external to processor 44 and also be used to generate the stimulating waveform. Typically, a 32 or 100 kilohertz crystal clock may be used to provide timing. Stimulation pulse width is typically 100 to 500 microseconds (10 to 50 oscillations of 100 kilohertz clock), and the pulse interval may be 25 milliseconds or 2500 oscillations. The "on time," i.e., the period in which the pulses are applied, may be two seconds (200,000 oscillations) for this waveform, and the "off time," i.e., the period in which no pulses are applied, may be three seconds. It is useful to synchronize time inside the processor 44. A programmable storage device, such as programmable calendar 48, may be used to keep track of different times during the treatment period, such as hours of the day, day of the week, etc.

Figure 6A:
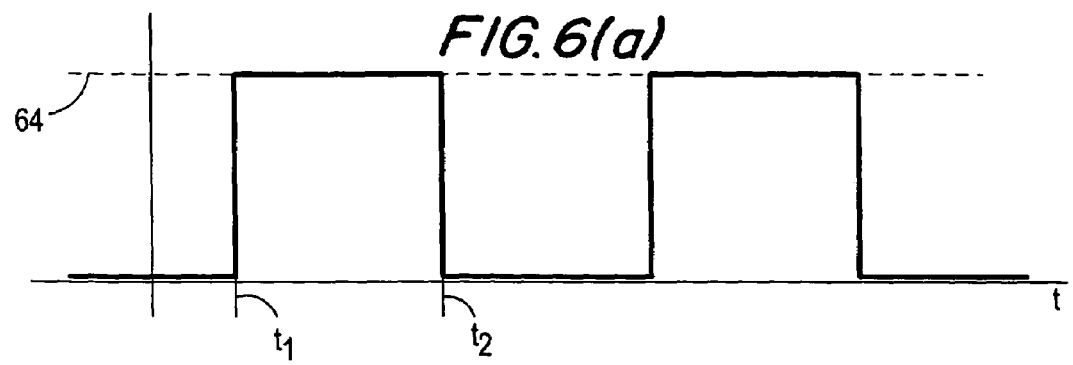
FIG. 6(*a*) is a time plot illustrating a current wave form in accordance with the invention.
Figure 6B:
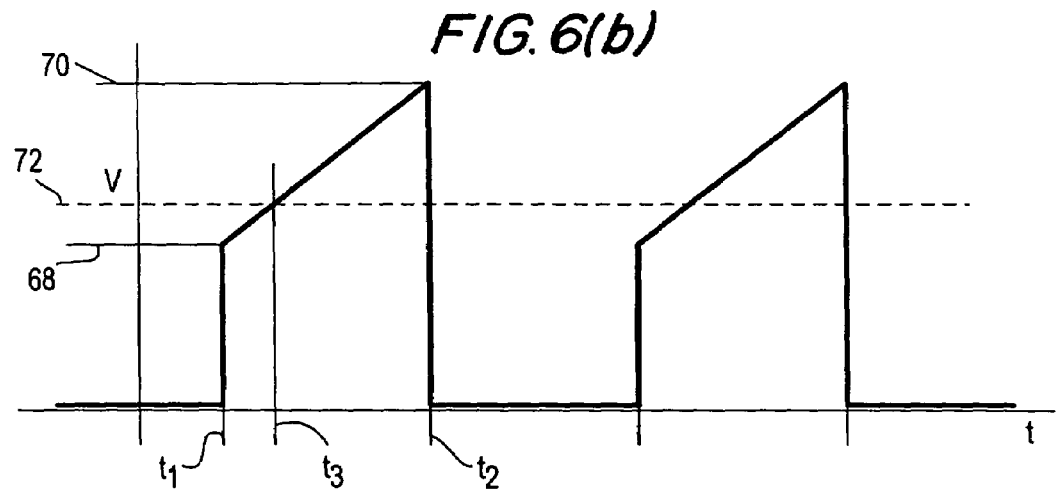
Figure 6C:
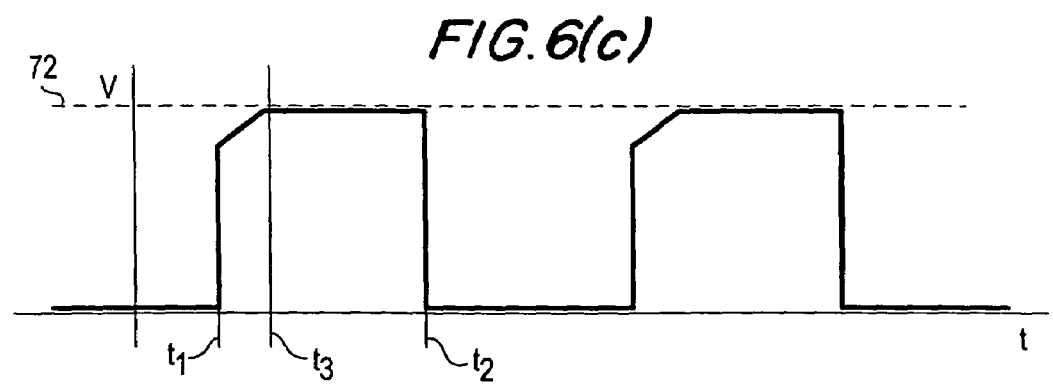

With continued reference to FIG. 2, the electrodes 16 (FIG. 1) present an impedance to the stimulating output leads 14 of I/V circuit 20. This impedance may be made up of two components. The first component is a resistance due to net energy transfer from circuit 20 to the stimulated tissue S, and the second component is a capacitance in series with the resistance due to ion transfer and charge accumulation across the electrode-tissue interface. FIGS. 6(a)-(c) illustrate the effects of these components. If a pulse of constant current is sent through electrodes 16, as illustrated in FIG. 6(a), the resistance component causes a voltage to immediately appear across the electrodes (FIG. 6(b)). As the current continues to flow during the pulse, the capacitance component charges up, which may contribute to a steady increase in voltage during the pulse. Both of these components may vary in value from patient to patient. For an individual patient, these values may also change after implantation due to factors such as, for example, location of electrode placement, shifts in placement, changes in physiological conditions at the tissue interface, changes in anatomical shape, etc.

For instance, an increase in capacitance may cause the voltage near the trailing edge of the constant current pulse to increase without any corresponding increase in stimulating strength. This in turn may cause increased energy to be delivered during the pulse, and thus a higher battery energy drain. In the case of a voltage pulse, a decrease in resistance may cause an increase in current at the leading edge of the pulse and attendant increased battery energy drain. Thus, the battery energy drain is limited in accordance with the invention by limiting the current and/or voltage during the stimulating pulse.

In a voltage pulse, which is typically generated by charging capacitor 28 to a peak value and turning on switch 32 to its maximum conductance, the initial peak current drain is only limited by switch conductance in series with the conductance of the lead system conductors 14.

I/V circuit 20 is capable of limiting high battery energy drain due to shifts in impedance. The closure of output switch 32 is controlled by sensor/controller unit 34. In the preferred embodiment, sensor/controller unit 34 provides a novel feature of sensing both the voltage across and the current through switch 32. Instructions on the shape and duration of the stimulating waveform are received from control circuit 24. The feedback controller in sensor/controller unit 34 compares the actual current 341 and/or voltage 342 of switch 32 to the wave shape instructions of control circuit 24. Based on the difference of these two signals, control circuit 24 produces an error signal to control switch 32 through negative feedback. These operations can be accomplished in either a digital or analog mode or in a combination thereof. The switch 32 is typically an analog device, and therefore signal 343, which is ultimately produced to control switch 32, may also be analog. The digital portion of this function could be accomplished in control circuit 24 with real-time digitized current and/or voltage data 261 supplied by sensor/controller unit 34.

Another feature of switch 32 working in conjunction with control circuit 24 is the ability to detect when the pulse wave form meets or exceeds a certain limit, or threshold, in voltage and/or current, to flag that occurrence as an "event," and to log or store the event at the time in which it occurred. This event marker, along with the time during the waveform, is available to control circuit 24 via line 261. Control circuit 24 may also be programmed to detect when the limit, or threshold, is reached during a particular part of the stimulating pulse, i.e., leading edge, trailing edge, etc.

Another feature in accordance with the present invention embodied in I/V circuit 20 is improved accuracy in the operation of voltage multiplier 26. An important novel feature is the added programmable parameter of a voltage and/or current limit or threshold value set by the clinician, in conjunction with the programmable value of either current or voltage, including the shape of the stimulating pulse (e.g., starting current and/or voltage, ending current and/or voltage, start time, stop time, duration, etc.).

The programmable current or voltage threshold parameter is stored with other programmable information in control circuit 24. An instruction based on this parameter is supplied to voltage multiplier 26 which is capable of charging capacitor 28 to a large number of voltages closely spaced in value. For example, the voltage multiplier 26 would be instructed by control circuit 24 to charge capacitor 28 to a voltage just slightly larger than the programmable voltage limit or threshold. The voltage multiplier 26 may also be used to control the wave shape in conjunction with sensor/controller unit 34.

The processor in control circuit 24 can adjust the voltage multiplier 26 to a lower voltage to achieve the programmed limiting and thus save battery power. The voltage multiplier 26, which may include a switch capacitor array, may increase or decrease the battery voltage $V_B$, e.g., in integer or half integer multiples thereof, such as $\frac{1}{2} V_B$, $\frac{3}{2} V_B$, $2 V_B$, $3 V_B$, etc. Alternatively, voltage multiplier 26 may be or may contain a transformer, usually in flyback mode, to change battery voltage $V_B$ in order to maintain the necessary voltage, e.g., such that $V_m > I_{program} * R_{electrode}$.

The embodiment of I/V circuit 20 allows for many programmable modes of operation including the modes of constant current and voltage discharge with switch 32 turned on to maximum conductance. One of the additional modes includes a constant current or a controlled-current wave shape with a separately programmable voltage limit or threshold. In this mode, the sensed current 341 may be used to regulate switch 32 through negative feedback. For example, the sensed voltage 342 is compared to the programmable voltage limit. If this sensed voltage 342 reaches this programmable voltage limit, the feedback may be modified to maintain the sensed voltage 342 at this limit. It is understood that the feedback may maintain the voltage at the limit, slightly below the limit, or prevent the voltage from exceeding the limit, as deemed appropriate by one skilled in the art. Another mode of operation is a constant voltage or controlled-voltage wave shape with a separately programmable current limit. In this mode, the sensed voltage 342 may be used to regulate switch 32 with negative feedback. The sensed current 341 is compared to the programmable current limit. If this sensed current 341 reaches the limit, the feedback may be modified to maintain current at this limit. Typically, the initial voltage on capacitor 28 may be set by control circuit 24 to be the minimum voltage required. For instance, if the constant current pulse is programmed to 10 milliamps and the greatest total impedance is 700 ohms, the initial voltage of capacitor 28 would be set at a voltage slightly above seven volts such that the voltage across capacitor 28 at the end of the pulse would be seven volts.

Certain modes of operation in accordance with the invention may not require the use of particular elements described in I/V circuit 20 with respect to FIG. 2. For example, in the case of constant current or a current-controlled wave shape, voltage limiting may also be achieved without voltage sensing means in control circuit 24 by charging capacitor 28 to the programmed voltage limit value. A limitation in voltage is achieved since the voltage across 28 is theoretically the maximum voltage that can appear across output 14. In this case, event detection (as described above) can be implemented by detecting saturation or the condition of maximum conductance of switch 32. In the case of voltage discharge with switch 32 turned on to maximum conductance, no voltage regulation is taking place and therefore the voltage sensing of 24 is not necessary. However, current sensing is implemented to limit current in this case.

Another feature of the preferred embodiment of IN circuit 20 is the ability of a stored program or subroutine in control circuit 24 to generate a sequence of current-controlled (and/or voltage-controlled) pulses associated with a sequence of voltage (and/or current) limit values, to interpret resulting limit event data, and to thereby measure the induced voltage (and/or current) waveform shape. The IN circuit 20 may store this shape for subsequent telemetry to the clinician, and analyze the shape to calculate impedance values, including resistance and/or capacitance components, as will be described in greater detail hereinbelow.

An additional aspect in accordance with the invention is the minimum energy capacity of battery 22. To achieve long term therapy, e.g., for a three to five year period, the energy limiting features described above are preferably combined with at least a 10 watt-hr total battery capacity. In the case of lithium type batteries the corresponding total deliverable current should preferably be three ampere hours.

Figure 4:
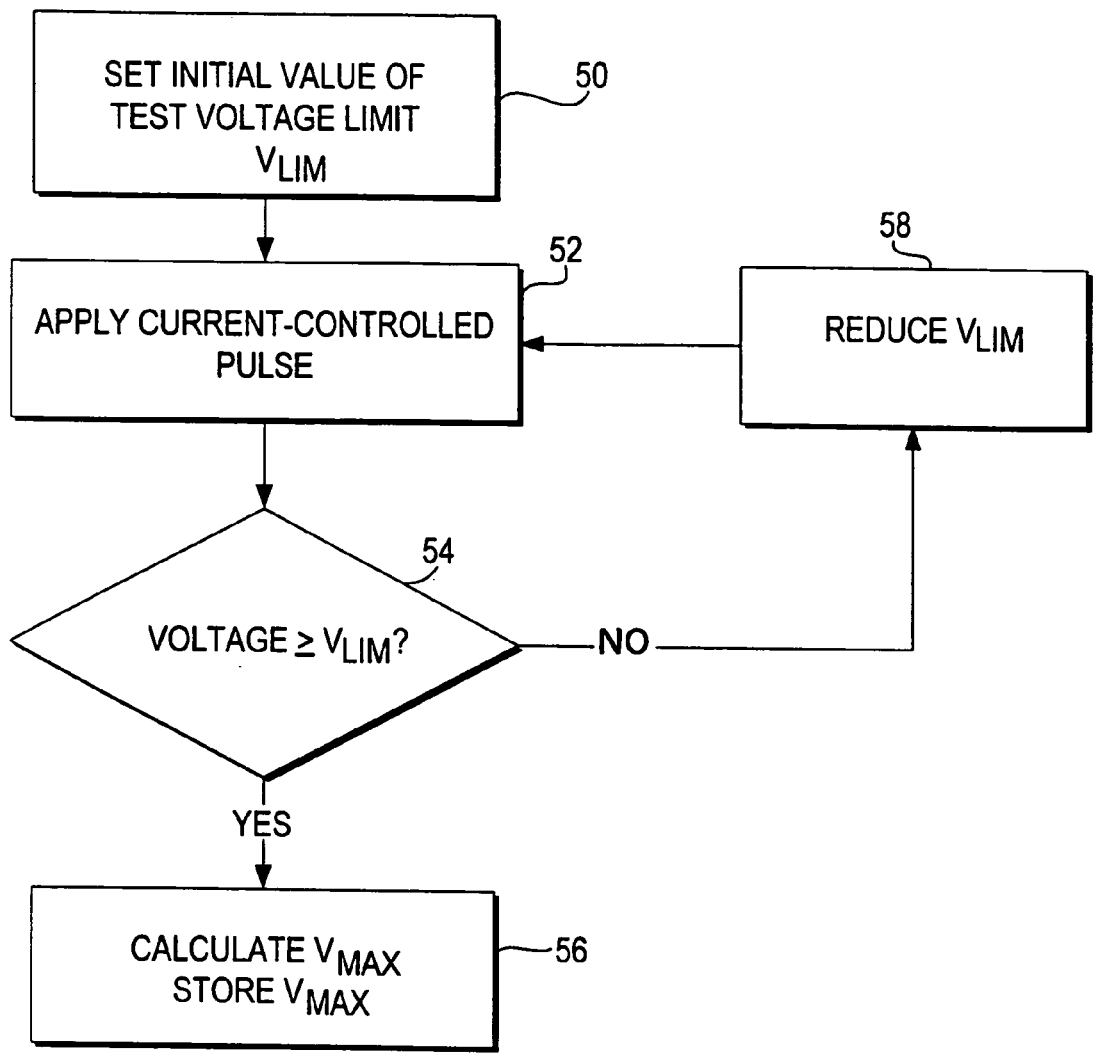
FIG. 4 is a flow chart of steps involved in creating a table of voltage threshold values and associated current values in accordance with the invention.

The operation of IN circuit 20 is described with respect to FIGS. 4, 5, and 6(a)-6(c). FIG. 4 illustrates a method for setting the values of the upper limit voltage $V_{max}$. As a result of performing the steps of FIG. 4, a data table associating current values with upper voltage limits or thresholds $V_{max}$ is compiled. The real-time clock is programmed to apply controlled-current values to the tissue at particular times during the treatment period. Upon implantation of the stimulator, the voltage for each programmed current value may be measured, and a voltage limit may be set for each current value. At step 50, an initial test voltage limit is set, i.e., $V_{lim}$. The current-controlled or constant current pulse is applied at step 14. If the voltage is found to meet or exceed $V_{lim}$ at step 54, the process proceeds to step 18. $V_{max}$ may be set equal to $V_{lim}$. Alternatively, $V_{max}$ is calculated as a value greater than the measured $V_{lim}$, e.g., 125% to 150% of the measured value. The calculated value of $V_{max}$ is stored, preferably in tabular form along with the associated current value, at step 18. If the voltage does not meet or exceed the present value of $V_{lim}$ at step 54, then $V_{lim}$ is reduced by a predetermined increment at step 58, and the process is repeated until the voltage exceeds the value of $V_{lim}$. This process is repeated for each current-controlled pulse value until all applicable values of $V_{max}$, are calculated and stored in a table. Alternatively, this process may be carried out for a voltage-controlled pulse in order to create a table of associated current limits. In such a case, an initial value of a test current limit would be set at step 50, and the voltage-controlled pulse applied at step 14. The sensed current would be compared with the test current limit at step 54. If the sensed current is found to meet or exceed the test current limit, a current limit may be set at step 18. If the sensed current does not meet or exceed the test current limit, the test current limit may be lowered at step 58, and the process of steps 14-58 repeated. This procedure for setting a table of current/voltage limits is exemplary only, and it is contemplated that other test procedures may be implemented.

Figure 5:
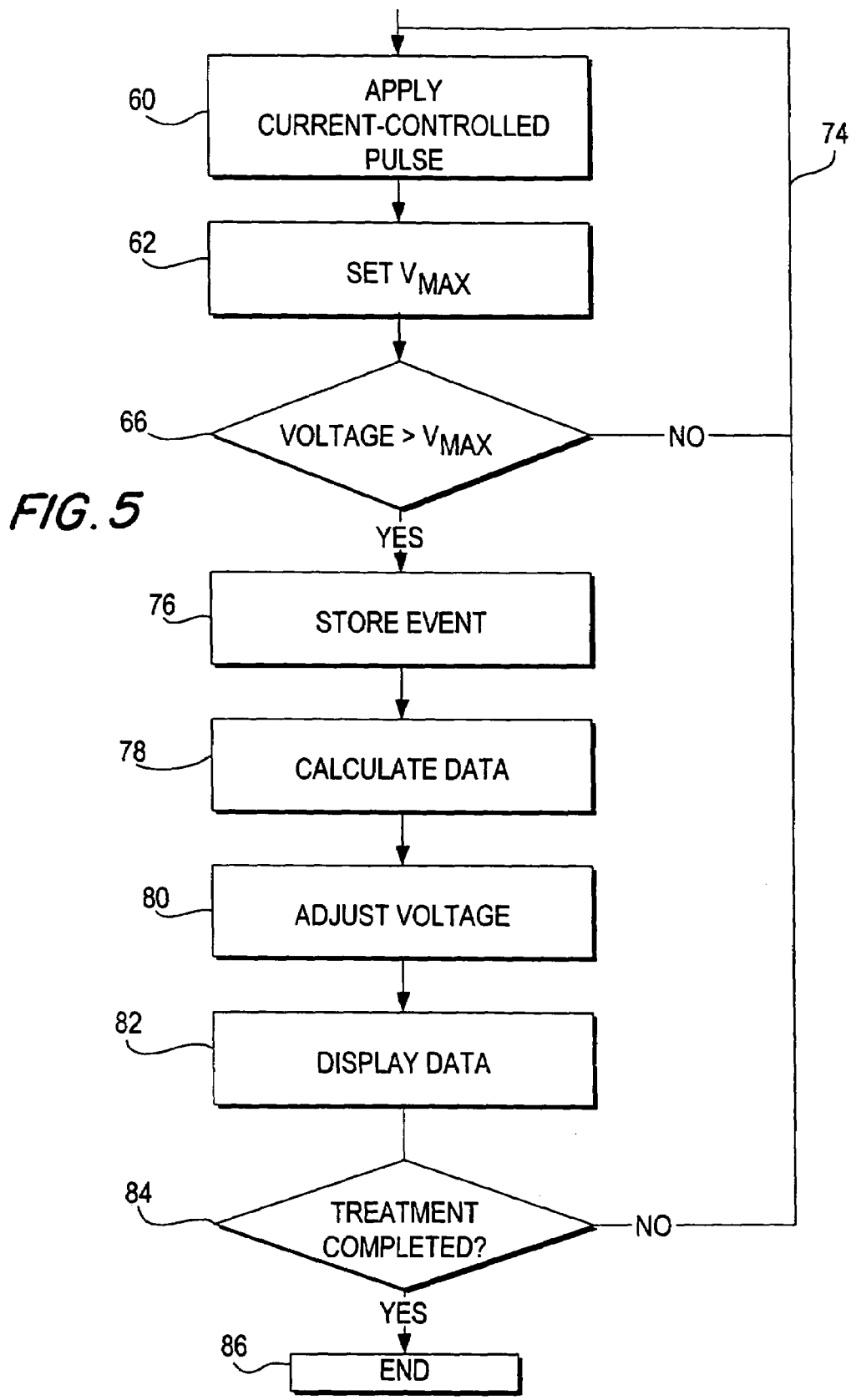
FIG. 5 is a flow chart of steps involved in comparing sensed voltage values with voltage threshold values in accordance with the invention.

FIG. 5, in conjunction with FIGS. 6(a)-6(c), illustrates the operation of the I/V circuit 20 in accordance with the invention during the application of a stimulation waveform to the tissue. The following exemplary procedure is described with respect to a current-controlled pulse with a programmed voltage threshold, but a similar procedure would be carried out for a voltage-controlled pulse with a current threshold.

At step 60, the current-controlled pulse may be applied to the stomach tissue. The sequencing of various electrical pulses is controlled by the control circuit 24, described above with respect to FIG. 2. As illustrated in a time plot in FIG. 6(a), the exemplary current pulse commences at t1 and ends at t2. (The durations of the various signals are not shown to scale and may have whatever duration is deemed appropriate to one skilled in the art.) Current-control switch 32 maintains current at the programmed current 64.

At step 62, a value is set for an upper voltage limit, i.e., $V_{max}$. The value of $V_{max}$, may be fixed. Alternatively, $V_{max}$ may be adjustable or programmable based on the circuit operating conditions, such as, for example, the magnitude of the current applied at step 60. A lookup of the tabular data compiled in FIG. 4 may be performed to set a value of $V_{max}$.

At step 66, the sensor/controller unit 34 measures sensed voltage and determines whether the voltage meets or exceeds the upper voltage limit $V_{max}$. The sensor/controller unit 34 may be programmed to measure continuously or periodically store voltage data telemetry at step 66. A time plot illustrating voltage V across the tissue is shown at FIG. 6(b). Due to the polarization capacitance effect of the stomach tissue, the voltage across the stomach tissue increases as the circuits attempts to maintain constant current. Thus, the voltage, initially at voltage 68 at t1, may increase to voltage 70 at t2. (FIGS. 6(a)-6(c) are aligned such that signals represented in the FIGS. in the same horizontal position occur simultaneously.) In FIG. 6(b), the voltage meets or exceeds voltage limit $V_{max}$ 72 at t3.

The comparison of the voltage with the voltage limit $V_{max}$ (step 66) may occur continuously during the stimulating pulse. Alternatively, the voltage sensor 34 may be programmed to compare the voltage with the voltage limit $V_{max}$ at the leading edge of the stimulating pulse, i.e., at a time period near t1. According to another alternative embodiment, the voltage sensor 34 may be programmed to determine if the voltage meets or exceeds $V_{max}$ at the trailing edge of the stimulating pulse, i.e., at a time period near t2.

If the voltage limit sensor 34 is not triggered, i.e., voltage is below voltage limit $V_{max}$, operation of the circuit proceeds on path 74 of the flowchart of FIG. 5, and the circuit applies a current pulse to the tissue, as required by the control circuit. Voltage limit $V_{max}$ may be set to a new value at step 62 if operating conditions require, e.g., if the current pulse changes.

However, if the voltage meets or exceeds voltage limit $V_{max}$, several operating steps may also occur. Steps 76, 78, 80, and 82 are illustrated in sequential order. However, it is understood that steps 76, 78, 80, and 82 are independent and may occur in a different order or simultaneously, as deemed appropriate by one skilled in the art. Certain ones of these steps may also be omitted, if desired to change the functionality of the circuit.

At step 76, the occurrence of the "event" described above, i.e., the occurrence of voltage meeting or exceeding the upper voltage limit $V_{max}$, is stored, e.g., in the memory of the control circuit. In the example of FIG. 6(b), the event occurred at time t3. The time associated with the event may be measured as an absolute time value, i.e., the calendar date and time, or as the elapsed time from the initiation of the treatment, or as the elapsed time from the initiation of the particular current pulse. The occurrence of the event may be included in telemetry data, as with the voltage data at step 66, above. The event data point may include the current value and the voltage at the time the event occurred, i.e., a "current value–voltage limit pair."

With continued reference to FIG. 5, data may be calculated at step 78. For example, the total lead resistance $R_{eff}$ may be calculated, for example, as the ratio of $V_{max}$ divided by the programmed current ($I_{prog}$). The event data point may also include associating the current value with the electrode lead resistance, i.e., as an "electrode resistance pair." This data point may also be stored in the telemetry data. Monitoring lead resistance is useful in predicting the battery life of the stimulator. As described above, increased resistance causes a substantial voltage drain on the battery, with associated reduction in battery life.

The polarization capacitance may also be calculated from the data taken during the above steps. For example, the polarization capacitance may be calculated as the ratio of the programmed current to the time rate of change of the voltage (i.e., $C_{polarization}=I_{prog}/dV/dt$). From the parameters being measured, the time rate of change of the voltage may be approximated from the change in voltage between the voltage 68 at the leading edge t1 and the voltage 70 at the trailing edge t2 of the pulse and the time elapsed during the pulse, or the pulse width (i.e., t2–t1). Calculation of the polarization capacitance provides information on battery drain, wherein a large capacitance may be indicative of high drain on the battery that reduces battery life. The event data point may also include associating the current value with the polarization capacitance. This data point may also be stored in the telemetry data.

At step 80, voltage may be adjusted by using the voltage multiplier 26. For example, the control circuit 24 may be programmed to adjust the voltage multiplier 26 to reduce voltage in integer or fractional integer increments. With reference to FIG. 6(c), after the event occurs at t3, the voltage is adjusted to remain at the level of voltage limit $V_{max}$ 72, slightly below voltage limit $V_{max}$ 72, or not to exceed $V_{max}$ 72.

The calculation of lead resistance and polarization capacitance at step 78 may be helpful in determining the degree of voltage adjustment in order to maintain the voltage below $V_{max}$. A large value of electrode resistance or polarization capacitance may indicate a substantial drain on the battery. Accordingly, a substantial adjustment may be made in the voltage at step 80. Conversely, smaller values of electrode resistance or polarization capacitance may indicate a less substantial drain on the battery, and a smaller adjustment to keep the voltage at or below $V_{max}$.

At step 82, the event data stored or calculated at steps 76-80 may be graphically displayed or listed on a display terminal or printed output. The process may continue until it is determined that the treatment is completed at step 84, at which time the current/voltage limitation may be ended (step 86).

As illustrated in FIG. 3, above, I/V Circuit 20 includes a real-time clock 46, which supplies data corresponding to the time of day during the treatment period, and programmable calendar 48, that can be programmed to store the parameters that define the above pulse train. The parameters are used by the control circuit 24 in determining the wave shape of the stimulating pulse. The parameters correspond to particular times during the treatment. Medical observations suggest that food intake, digestion and other gastrointestinal functions are circadian, that is, they operate on a 24 hour daily cycle. There are certain periods during the day when gastric functions are less active than other times of the day. The programmable calendar 48 can therefore provide increased stimulation at certain hours of the day, and decreased stimulation at other hours of the day. Among other benefits, device longevity may be increased due to the energy saving of this programming. Thus the stimulators 12 may deliver stimulation pulses for a fraction of each hour while the patient is awake. The programmability of calendar 48, described below, allows the application of longer-term circadian variations which may likewise be beneficial to the patient and extend battery life.

Figure 7:
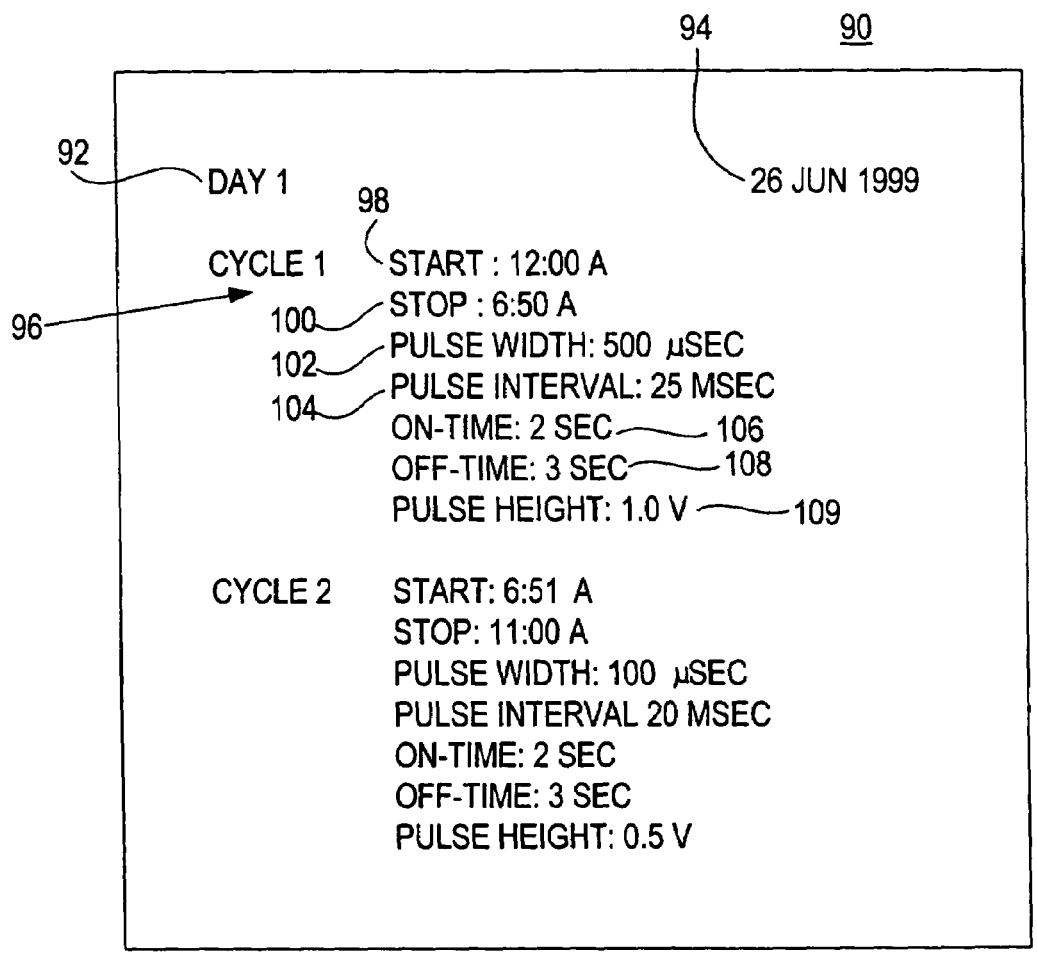
FIG. 7 illustrates a data structure for storing parameters for the waveform of a stimulating pulse in accordance with the invention.

A plurality of pulse train parameters may be stored in memory associated with the programmable calendar 48. Sample data 90 for a treatment period is shown in FIG. 7. The data 90 may be for a 24-hour period, such as "day one" 92, which may include calendar information 94. The pulse trains may be stored as cycles 96. For example, pulse train parameters may include start times 98, stop times 100, the pulsewidth 102, the pulse interval 104, the duration of the applied pulses (the "on" period) 106, or the duration period in which no pulses are applied (the "off" period) 108, and the voltage of the pulse or the pulse height 109. The programmable calendar 48 receives data from the clock 46 concerning the time-of-day and the date. Programmable calendar 48 can obtain the associated parameters from the data 90 and supply them the processor 44, accordingly. The "date" associated with the treatment may vary, depending on the expected duration of the treatment. For example, in data format 110 (FIG. 8), the data may correspond to the day of week (e.g., "day one" 112 through "day seven" 114). Each of the data points in day one 112 through day seven is similar to data point 90. The programmable calendar 48 may function on a seven-day cycle wherein programmable calendar accesses day one after day seven in a continuous loop 116. Thus, each day of the week could have a particular sequence of stimulating pulse train parameters. As a result, the pulse train is programmed to stimulate the stomach tissue in the same way on the same day of each week.

Figure 10:
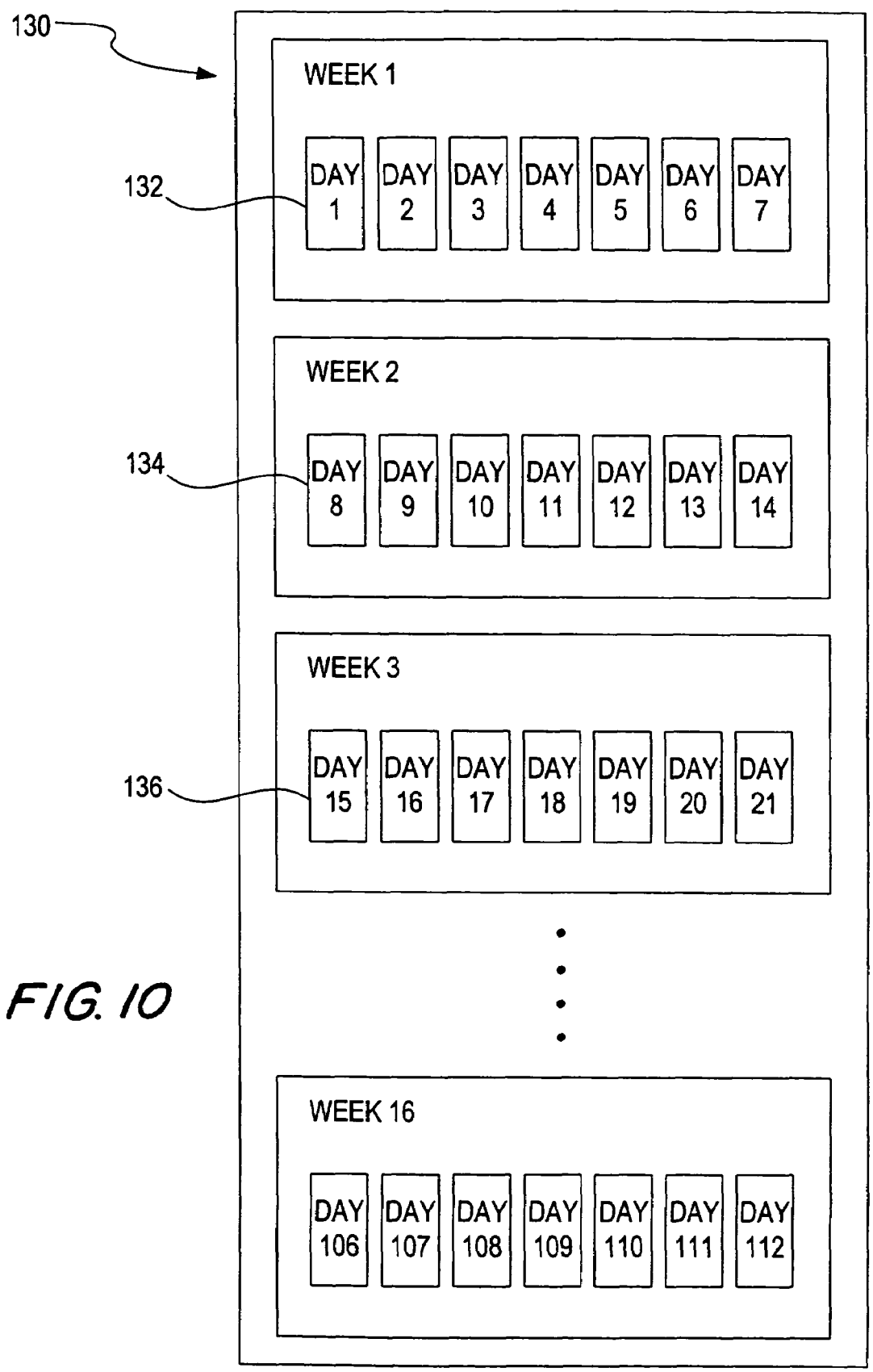
FIG. 10 illustrates another data structure in accordance with the invention.

As illustrated in FIG. 9, the data format 120 may refer to a simple, numbered day in a periodic sequence of days, such as the numbered days of the year (i.e., "day one" 122 through day 365" 124), or the numbered days within a month (e.g., "day one" 112 through "day 31", not shown). The calendar 48 would then cycle back to the first data point as indicated by arrow 126. As illustrated in FIG. 10, the data format 130 may be hierarchical and thus may recognize intermediate time periods, such as weeks 132 and/or months (not shown) within a treatment period. For example, it may recognize that the treatment is at "week two" 134 or "week three" 136, in addition to the elapsed number of days. The calendar 48 could be programmed to so that the pulse generator 10 is turned off for a number of weeks. The generator may then be turned on one day a week, During the next week, the generator may be turned on for two days a week, etc. Each sequence of cycles (see, FIG. 7) within a given "on" day, could also be different from the previous "on" day.

The programmability of the pulse train wave forms based on the date provides the ability to turn the above stimulating pulse train on or off or increase or decrease waveform parameters over increasingly longer meshed periods of time.

An alternative embodiment of the neuromuscular stimulator described above includes an additional mode for stimulating the neuromuscular tissue of the gastrointestinal tract. The neuromuscular stimulator applies a series of primary electrical pulses to the tissue as described hereinabove. These electrical pulses may be applied during a first time interval, and may be discontinued during a second time interval. A secondary series of pulses having a lower voltage may be applied to the tissue during the second time interval, i.e., when the primary electrical pulses are discontinued. The resulting current flowing between the stimulating electrode pair is measured.

Data, including, for example, sensed current, may be measured. The current data may be analyzed for changes over time. From this analysis, statistics may be computed. For example, a statistic which may be computed is the time period in which the changes in the current data repeats. This time period may be used to approximate the peristaltic action of the tissue. It may be desirable to change the rate of peristaltic activity, i.e., to slow down or increase the rate thereof, by varying the series of electrical pulses based on the statistics as described above.

The foregoing is merely illustrative of the principles of this invention and various modifications can be made by those skilled in the art without departing from the scope and spirit of the invention.

What is claimed is:

1. A neuromuscular stimulator for stimulating tissue of the gastrointestinal tract with a series of electrical pulses applied to the neuromuscular tissue during a treatment period, comprising:
a real time clock configured to supply data corresponding to the time of day during the treatment period;
a programmable calendar configured to store a parameter for defining said series of electrical pulses, the parameter having a reference to a respective time of day during the treatment period;
a control circuit configured to apply said series of electrical pulses defined by the parameter at the respective time of day.

2. The neuromuscular stimulator defined in claim 1, wherein the parameter is a time period during which said series of electrical pulses are applied to the neuromuscular tissue.

3. The neuromuscular stimulator defined in claim 2, wherein the time period comprises a start time with reference to the time of day and a duration with respect to the start time, and wherein the control circuit is configured to apply the series of electrical pulses beginning at the start time and extending for the duration.

4. The neuromuscular stimulator defined in claim 2, wherein the time period comprises a start time with reference to the time of day, a first duration with respect to the start time, and a second duration with respect to the first duration, and wherein the control circuit is configured to apply the series of electrical pulses beginning at the start time and continuing for the first duration, and discontinuing the series of electrical pulses during the second duration.

5. The neuromuscular stimulator defined in claim 2, wherein the time period comprises a first time with reference to the time of day and a second time with reference to the time of day, and wherein the control circuit is configured to apply the series of electrical pulses beginning at the first time and discontinuing the series of electrical pulses at the second time.

6. The neuromuscular stimulator defined in claim 1, wherein the parameter is a time period corresponding to the pulse width for each pulse in the series of electrical pulses.

7. The neuromuscular stimulator defined in claim 1, wherein the parameter is a time period corresponding to the pulse interval between each pulse in the series of electrical pulses.

8. The neuromuscular stimulator defined in claim 1, wherein the parameter is a voltage corresponding to the pulse height for each pulse in the series of electrical pulses.

9. The neuromuscular stimulator defined in claim 1, wherein the real time clock is configured to supply data corresponding to a week during said treatment period.

10. The neuromuscular stimulator defined in claim 1, wherein the real time clock is configured to supply data corresponding to a day of the week during said treatment period.

11. The neuromuscular stimulator defined in claim 1, wherein the real time clock is configured to supply data corresponding to the month of the year during said treatment period.

12. The neuromuscular stimulator defined in claim 11, wherein the real time clock is configured to supply data corresponding to a day of the month during said treatment period.

13. The neuromuscular stimulator defined in claim 1, wherein the real time clock is configured to supply data corresponding to a day of the year during said treatment period.

14. A method of stimulating neuromuscular tissue of the gastrointestinal tract with a series of electrical pulses applied to the neuromuscular tissue during a treatment period, comprising:
   supplying data corresponding to the time of day during the treatment period;
   storing a parameter for defining said series of electrical pulses, the parameter having a reference to a respective time of day during the treatment period; and
   applying said series of electrical pulses defined by the parameter at the respective time of day.

15. The method defined in claim 14, wherein supplying the time of day comprises:
   providing a real time clock.

16. The method defined in claim 14, wherein storing the parameter further comprises:
   providing a programmable calendar for storing the parameter.

17. The method defined in claim 14, wherein storing the parameter further comprises:
   storing the parameter on the programmable calendar.

18. The method defined in claim 14, wherein the parameter is a time period, and wherein the storing the parameter further comprises:
   storing the time period during which said series of electrical pulses are applied to the neuromuscular tissue.

19. The method defined in claim 18, wherein the storing the time period comprises:
   storing a start time with reference to the time of day, and storing a duration with respect to the start time; and
   applying the series of electrical pulses beginning at the start time and extending for the duration.

20. The method defined in claim 18, wherein the storing the time period comprises:
   storing a start time with reference to the time of day, storing a first duration with respect to the start time, and storing a second duration with respect to the first duration; and
   applying the series of electrical pulses beginning at the start time and continuing for the first duration, and discontinuing the series of electrical pulses during the second duration.

21. The method defined in claim 18, wherein the storing the time period comprises:
   storing a first time with reference to the time of day, and storing a second time with reference to the time of day; and
   applying the series of electrical pulses beginning at the first time and discontinuing the series of electrical pulses at the second time.

22. The method defined in claim 18, wherein the parameter is a time period, and wherein the storing the parameter further comprises:
   storing the time period corresponding to the pulse width for each pulse in the series of electrical pulses.

23. The method defined in claim 18, wherein the parameter is a time period, and wherein the storing the parameter further comprises:
   storing the time period corresponding to the pulse interval between each pulse in the series of electrical pulses.

24. The method defined in claim 18, wherein the parameter is a voltage, and wherein the storing the parameter further comprises:
   storing the voltage corresponding to the pulse height for each pulse in the series of electrical pulses.

25. The method defined in claim 14, wherein the supplying data corresponding to the time of day further comprises:
   supplying data corresponding to a week during said treatment period.

26. The method defined in claim 25, wherein the supplying data corresponding to the time of day further comprises:
   supplying data corresponding to a day of the week during said treatment period.

27. The method defined in claim 14, wherein the supplying data corresponding to the time of day further comprises:
   supplying data corresponding to the month of the year during said treatment period.

28. The method defined in claim 27, wherein the supplying data corresponding to the month of the year further comprises:
   supplying data corresponding to the day of the month during said treatment period.

29. The method defined in claim 14, wherein the supplying data corresponding to the time of day further comprises:
   supplying data corresponding to the day of the year during said treatment period.

* * * * *